United States Patent [19]
McLaughlin et al.

[11] Patent Number: 5,522,525
[45] Date of Patent: Jun. 4, 1996

[54] MEDICATION DISPENSER STATION

[75] Inventors: John T. McLaughlin, Corona Delmar; Arthur E. Brown, Escondido, both of Calif.

[73] Assignee: Nu-Box, Inc., Irvine, Calif.

[21] Appl. No.: 348,593

[22] Filed: Dec. 2, 1994

[51] Int. Cl.$^6$ .................................................. G07F 11/00
[52] U.S. Cl. .................................. 221/4; 221/15; 221/82
[58] Field of Search .............................. 221/2, 4, 5, 7, 221/9, 15, 82, 86, 197, 13

[56] References Cited

U.S. PATENT DOCUMENTS

| | | | |
|---|---|---|---|
| 2,512,961 | 6/1950 | Morrison | 62/141 |
| 2,792,147 | 5/1953 | Stewart | 221/3 |
| 3,638,688 | 2/1972 | Conklin et al. | 364/479 |
| 3,727,794 | 4/1973 | DiEranco | 221/3 |
| 3,762,601 | 10/1973 | McLaughlin | 221/2 |
| 3,822,004 | 7/1974 | Bolen, Jr. | 194/15 |
| 3,998,356 | 12/1976 | Christensen | 221/2 |
| 4,207,992 | 6/1980 | Brown | 221/15 |
| 4,473,884 | 9/1984 | Behl | 364/479 |
| 4,512,500 | 4/1985 | Belbin, Sr. | 221/82 |
| 4,572,403 | 2/1986 | Benaroya | 221/3 |
| 4,573,606 | 3/1986 | Lewis et al. | 221/2 |
| 4,598,742 | 7/1986 | Taylor | 141/95 |
| 4,695,954 | 9/1987 | Rose et al. | 364/413 |
| 4,747,514 | 5/1988 | Stone | 221/4 |
| 4,809,877 | 3/1989 | Albright | 221/82 |
| 4,811,764 | 3/1989 | McLaughlin | 141/98 |
| 4,847,764 | 7/1989 | Halvorson | 364/413.02 |
| 4,885,357 | 12/1989 | Larkins et al. | 530/373 |
| 4,911,327 | 3/1990 | Shepard et al. | 221/15 |
| 4,953,745 | 9/1990 | Rowlett, Jr. | 221/5 |
| 5,272,321 | 12/1993 | Otsuka et al. | 221/2 |

FOREIGN PATENT DOCUMENTS

0285675A1 10/1988 European Pat. Off. .

OTHER PUBLICATIONS

Cregg, James M., Vedvick, Thomas S. and Raschke, William C. (1993) Recent Advances in the Expression of Foreign Genes in *Pichia pastoris*. Bio Technology 11:905–909.

Marks, M. David and Larkins, Brian A. (1982) Analysis of Sequence Microheterogeneity among Zein Messenger RNAs. *J. of Biol. Chem.* 257(17): 9976–9983.

Scriver, Charles R., Kaufman, Seymour, Eisensmith, Randy C., and Woo, Savio L. C. (1995) The Hyperphenylalaninemias in *The Metabolic Basis of Inherited Disease*, (Scriver, C. S., et al., eds.) McGraw-Hill, Inc. New York, pp. 1015–1075.

Acosta, P., (1989) Nutrition Support of Children, Adolescents and Adults With Phenylketonuria (PKU) in *Nutrition Support Protocols*, (K. V. Sproat, C. Russell, eds.) Ross Laboratories, Columbus, pp. 9–17.

(List continued on next page.)

*Primary Examiner*—Kenneth Noland
*Attorney, Agent, or Firm*—Kelly Bauersfeld & Lowry

[57] ABSTRACT

A medication dispenser station is provided for automatic dispensing of medication in accordance with a prescription schedule for a patient. The station receives and supports a plurality of medication-containing cassettes in a vertical stack, with the cassettes having aligned discharge openings defining an open discharge chute. The cassettes, which may contain different medications to be administered at different times, includes scannable data identifying the medication and prescription schedule applicable to each cassette. A station read head scans the data to input information regarding the medication and administration schedule for each cassette to a station control unit. The control unit thereafter operates a station dispense head to engage the cassettes in a manner dispensing the medication via the discharge chute at the prescribed times. The thus-dispensed medication falls through the chute to an externally accessible receiver from which the medication can be removed by the patient.

23 Claims, 6 Drawing Sheets

OTHER PUBLICATIONS

Acosta, P., and Yannicelli, S. (1993) Nutrition Support of Infants, Children and Adults in *Nutrition Support Protocols,* (Cameron, A., C. Russell, eds.) Ross Laboratories, Columbus, pp. 1–16.

Prat, S. Cortadas, J., Puigdomenech, P. and Palau, J. (1985) Nucleic Acid (cDNA) and Amio Acid Sequences of the Maize Endosperm Protein Glutelin–2. *Nucleic Acids Res.* 13 (5): 1493–1504.

Wang, S–Z. and Esen, A. (1986) Priimary Structure of a Proline–Rich Zein and Its cDNA. *Plant Physiol.* 81: 70–74.

Thompson G. A. and Larkins B. A. (1989) Structural Elements Regulating Zein Gene Expression. *BioEssays* 10 (4): 108–113.

Osborne, T. B. (1908) Our Present Knowledge of Plant Proteins. *Science* 28 (718): 417–427.

Esen, A. (1986) Separation of Alcohol–Soluble Proteins (Zeins) from Maize into Three Fractions by Differential Solubility. *Plant Physiology* 80: 623–627.

Zein (1989) in *1990, USP XXII, NF XVII The United States Pharmacopeia, The National Formulary,* The United States Pharmacopeial Convention, Inc., p. 1997.

WHO (World Health Organization). (1985) Energy and Protein Requirements. Report of a Joint FAO/WHO/UNU Expert Consultation. Technical Report Series 724. World Health Organization, Geneva. p. 65.

Wang. S. and Esen, A. (1985) Expression of Maize Prolamins in *Escherichia coli. Plant Science* 42: 49–54.

Penrose, L., and Quastel, J. H. (1937) Metabolic Studies in phyenylketonuria. *Biochem J.* 31: 266–74.

Bickel, H., Gerard, J., and Hickman, E. M. (1953) Influence of Phenylalanine Intake on Phenylketonuria. *Lancet* (Oct. 17): 812–13.

Prat, Salome, Perez–Grau, Lluis and Puigdomenech, Pere (1987) Multiple Variability in the Sequence of a Family of Maize Endosperm Proteins. *Gene:* 52(1987) 41–49.

Pedersen, Karl, Devereux, John, Wilson, Deborah R., Sheldon, Edward and Larkins, Brian A. (1982) Cloning and Sequence Analysis Reveal Structural Variation among Related Zein Genes in Maize. *Cell,* 29: 1015–1026.

Folling, Asbjorn (1934) Uber Ausscheidung von Phenylbrenztraubensaure in den Harn also Stoffwechselanomalie in Verbindung mit Imbezillitat, *Hoppe–Seylor's Z. Physiol–Chem.,* 227, pp. 169–176.

FIG. 12

MEDICATION DISPENSER STATION

BACKGROUND OF THE INVENTION

This invention relates generally to apparatus for use in dispensing medication, particularly in tablet or capsule form or the like for administration to a patient. More specifically, this invention relates to an improved and relatively simplified medication dispenser station designed for automatic dispensing of one or more medications in accordance with prescription schedules.

A wide variety of automatic and/or programmable medication dispensing devices are known in the art, wherein one or more medications are dispensed for administration to a patient or patients in a timely manner. Some of these dispenser stations have been designed for use in a hospital or similar environment, wherein the station is typically adapted for safe storage of a large stock of different medications for a plurality of patients located, for example, on a common hospital floor. Other dispenser devices have been designed for use by an individual patient, such as at patient bedside in a hospital or convalescent facility, or for use in an in-home environment. The present invention is directed to an improved and relatively simplified medication dispenser station intended primarily for use by a single patient.

In general terms, medication dispenser stations designed for single patient use have been adapted to receive one or more medication-containing cassettes or cartridges which have been preloaded with a prescribed medication at a pharmacy. The medication-containing cassette or cassettes are transported to and loaded within the dispenser station. A station control unit is then operated, typically by use of a keypad or the like to instruct or program the station regarding the specific medications loaded therein and the applicable prescription and/or dispensing schedules. Inaccurate programming of the station will result in medication dispensing errors. This potential for dispensing errors has limited the market for medication dispensers of this type, particularly in the case of medication dispensers for in-home use wherein the station is typically programmed by the patient.

The present invention provides a significant improvement in medication dispenser stations by providing means for automatically programming a station control unit in response to loading of one or more medication-containing cassettes therein, whereby subsequent medication dispensing errors are substantially eliminated.

SUMMARY OF THE INVENTION

In accordance with the invention, an improved medication dispenser station includes a vertical column or tower for receiving and supporting a plurality of medication-containing cassettes which are individually preloaded with medication, typically in tablet or capsule form. A station read head is provided to read scannable data on the cassettes pertaining to medication type and prescription schedule, and to input such information to a station control unit. The station control unit thereafter operates a station dispense head to dispense medications from the cassettes in accordance with the appropriate prescription schedule.

In the preferred form, each cassette comprises a shallow tray having a rotatable carousel therein defining a circular array of medication-receiving pockets. The carousel for each cassette is partially exposed at the inner diameter of the cassette for engagement by the station dispense head. The dispense head includes means for moving the head vertically within the tower, and for radial displacement into engagement with the rotatable carousel of a selected medication-containing cassette. The dispense head rotates or indexes the carousel through a short rotational step, sufficient to sweep the medication within one of the pockets to a vertically open discharge chute for dispensing. A receiver is located at the bottom of the discharge chute and permits external access to the dispensed medication.

When the medication-containing cassettes are loaded onto the vertical tower, the station control unit is programmed to operate the station read head for purposes of reading the scannable data on each cassette. The preferred read head comprises an optical scanner with drive means for vertically displacing said scanner within the vertical tower to detect and read the scannable data at the inner diameter of each cassette. The scannable data may be provided in the form of bar code data.

The discharge chute is formed, in accordance with the preferred embodiment of the invention, by vertically aligned discharge openings formed in the cassettes of the vertical stack. The receiver includes a dispense detector such as a pressure sensor for detecting impact of a medication tablet or capsule thereon, thereby confirming that medication dispensing has occurred. The receiver may also include an access detector for determining that medication within the receiver has been accessed for administration to the patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
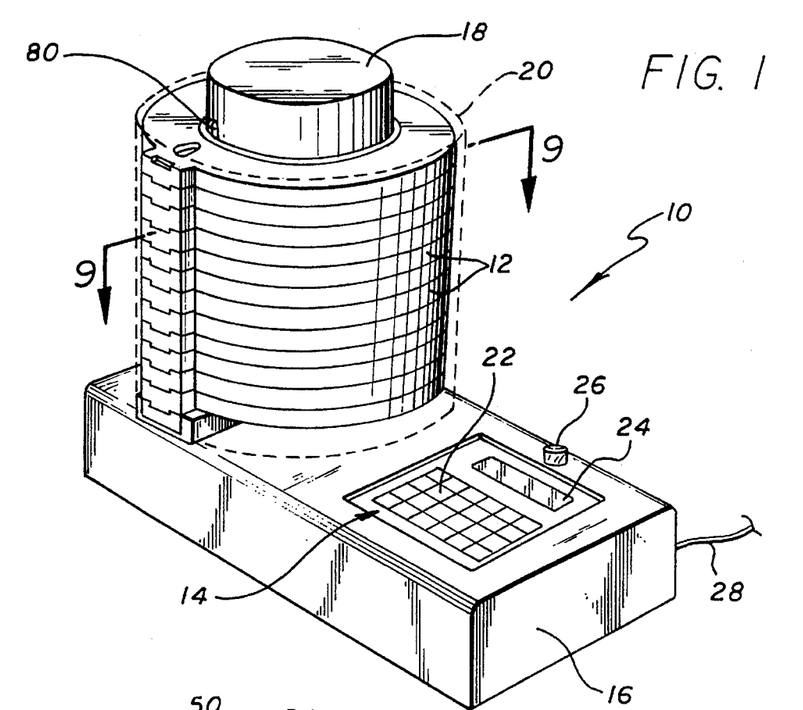
FIG. 1 is a perspective view illustrating a medication dispenser station embodying the novel features of the invention.

As shown in the exemplary drawings, an improved medication dispenser station referred to generally by the reference numeral 10 in FIG. 1 is provided for controlled dispensing of one or more medications, particularly such as prescription tablets or capsules. The dispenser station 10 receives and supports a plurality of medication-containing cassettes 12 in a vertical stack, wherein each cassette is preloaded with a selected medication. The dispenser station 10, including the cassettes 12, has means for automatically identifying the medications contained within the cassettes, and for determining the prescription dispensing schedule associated therewith, and for thereafter dispensing said medications in accordance with said schedule.

The improved medication dispenser 10 of the present invention is particularly designed for automatic dispensing of medications for administration to a single patient. In this regard, the station 10 is adapted for use at patient bedside or the like, and particularly for use in an in-home or similar environment. The multiple cassettes 12 are individually preloaded with appropriate medications by expert personnel or by automated means (not shown), for example, in a pharmacy by trained pharmacy personnel. The cassettes 12 are installed on or in the station 10 in a vertical stack in a simple manner which can be performed by the individual patient, without special supervision or programming. The thus-installed cassettes interface with a station control unit 14 to program the station automatically, and thereafter to dispense the medications in accordance with the appropriate dispensing schedule.

As shown in FIG. 1, the illustrative dispenser station 10 includes a relatively compact base 16 which has an upstanding cassette support tower 18 mounted at one side thereof. The cassette tower 18 has a generally circular cross sectional shape with a size to permit slide-on installation of a plurality of ring-shaped medication cassettes 12. A removable cover 20 (shown in dotted lines in FIG. 1) may be provided to cover and conceal the cassette stack from view, and lock means (not shown) may be provided for releasibly locking the cover onto the base 16 and thereby prevent unauthorized access to the medication-containing cassettes.

The control unit 14 includes computer memory elements mounted within the base 16. A keypad 22 is provided on the base 16 for use in inputting or downloading data from the control unit 14. An alpha-numeric display 24 is associated with the keypad 22, and a visual alarm 26 is provided to indicate, for example, when medication has been dispensed. An audible alarm (not shown) may also be provided in lieu of or in addition to the visual alarm 26. Electrical power may be supplied as needed to the dispenser station 10 by means of a power cord 28.

Figures 5, 6, 7:
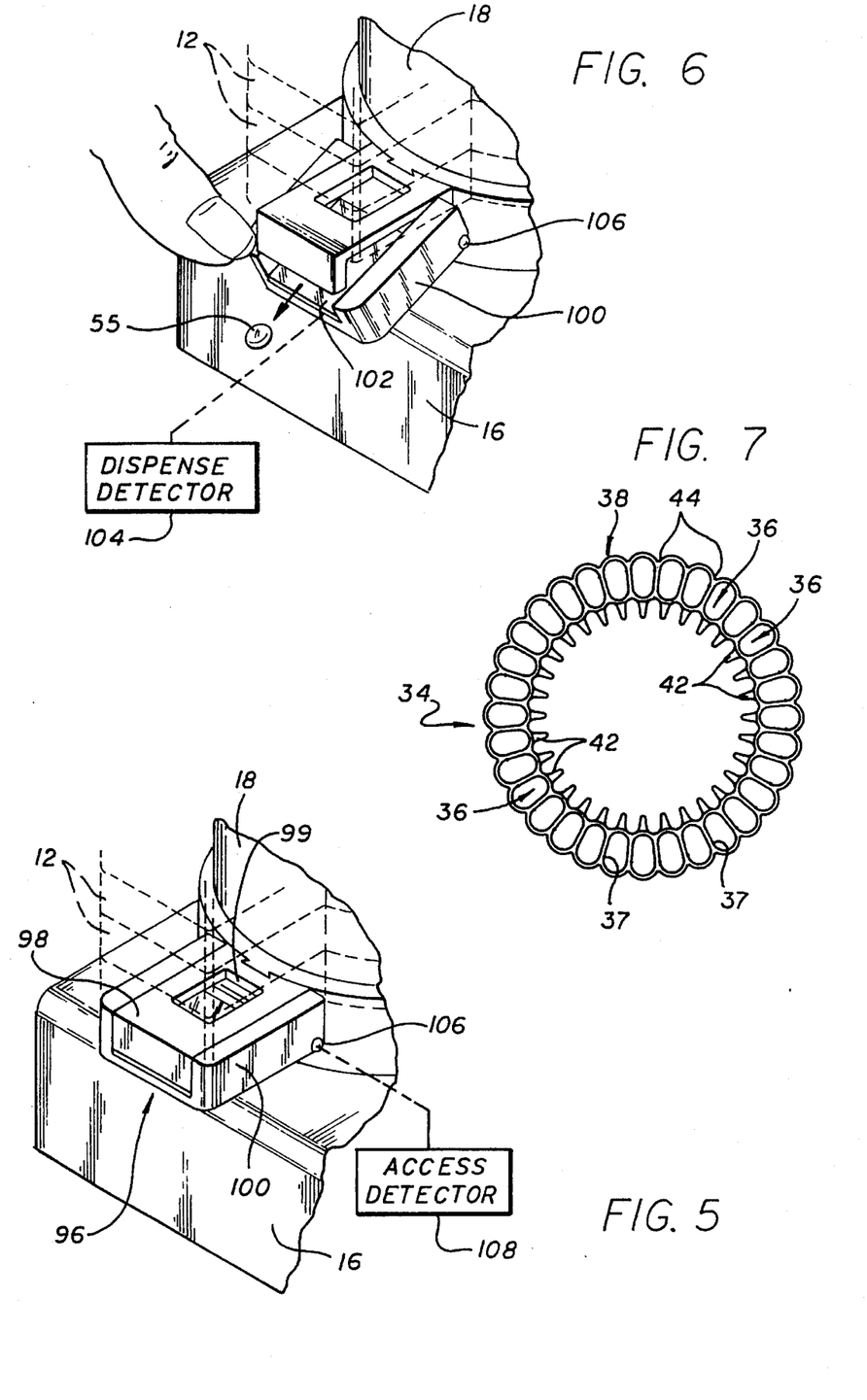
FIG. 5 is an enlarged fragmented perspective view of a portion of the dispenser station, and showing a medication receiver.
FIG. 6 is a fragmented perspective view similar to FIG. 5, and illustrating removal of medication from the receiver.
FIG. 7 is a plan view of a rotatable carousel forming a portion of the medication-containing cassette of FIG. 3.

The cassettes are shown in more detail in FIGS. 3, 4, 7, and 9–12. As shown, each cassette comprises an assembled pair of generally ring-shaped plastic housing members 30 and 32 (FIG. 10) defining an annular chamber therebetween. A rotatable carousel 34 is mounted within this chamber, between the housing members 30 and 32. As shown in FIG. 7, carousel 34 has a generally ring-shaped construction defining a circular array of vertically open pockets 36 separated by radial walls 37. The outer periphery of the carousel 34 has a discontinuous scalloped-edge configuration, as indicated by numeral 38 in FIG. 7, whereas the inner periphery includes a plurality of radially inwardly protruding drive teeth 42. As shown in FIG. 7, a single drive tooth 42 is provided for each associated pocket 36, and adjacent pockets 36 are separated at the scalloped outer periphery by a shallow recess or detent 44.

The carousel 34 is slidably and rotatably mounted between the cassette housing members 30, 32, with the drive teeth 42 projecting into and being exposed within a slot 46 at the inner periphery of the cassette. These drive teeth 42 are thus positioned for driving engagement with a station dispense head 48, as will be described in more detail. In addition, the drive teeth 42 are disposed adjacent to an inner ring 50 of the cassette, wherein this inner ring defines a surface onto which scannable data 54 such as bar code data or the like (FIG. 3) can be mounted or otherwise placed by imprinting or the like. This scannable data 54 provides machine readable information regarding the medication loaded into each cassette 12 and the prescription schedule associated therewith.

Each cassette 12 is preloaded at a pharmacy or the like, with a single medication tablet or dose 55 loaded into each pocket 36 of the rotatable carousel 34. In this regard, the illustrative drawings show the carousel with a total of 32 pockets 36 although it will be understood that different pocket configurations can be provided.

The housing members 30, 32 defining each cassette 12 have aligned ports 56 formed therein at the front of each cassette, thereby forming a vertically open passage therethrough. A spring 58 (FIG. 9) is mounted within the cassette at a location adjacent the ports 56. This spring reacts between the cassette housing members and the detents 44 of the carousel 34, with a leg 60 extending into an adjacent detent 44, to releasibly retain one of the carousel pockets 36 in vertical alignment with the cassette ports 56.

Figures 3, 4:
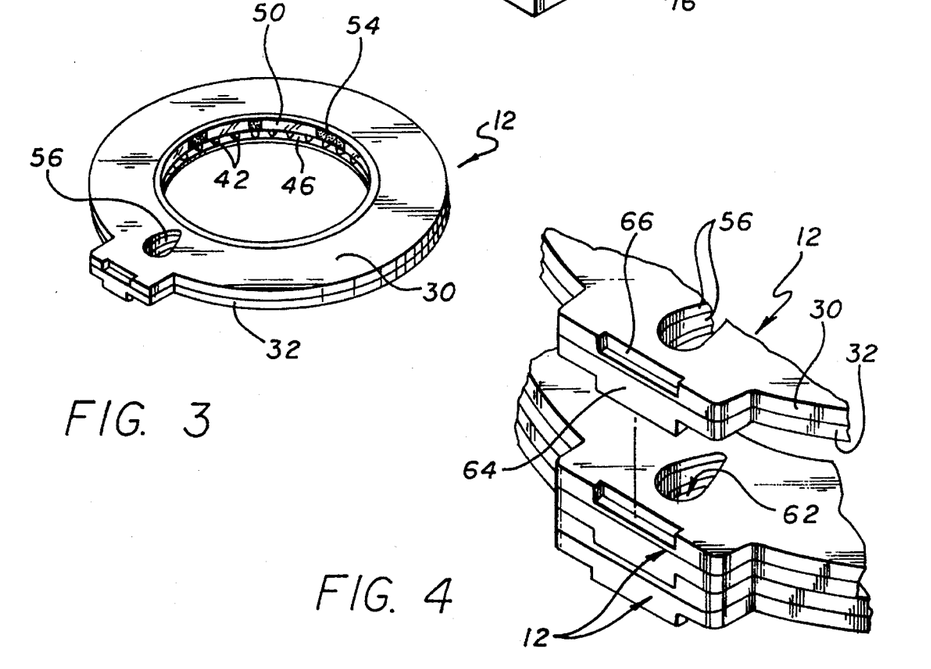
FIG. 3 is a perspective view of a medication-containing cassette for use in the invention.
FIG. 4 is a fragmented exploded perspective view illustrating a plurality of cassettes of FIG. 3 arranged in a vertically aligned stack.

When multiple cassettes 12 are installed on the tower 18 in a vertical stack, the cassette ports 56 of the multiple cassettes cooperate with the pockets 36 aligned therewith to define an open vertical chute 62 through which the medication is dispensed. In this regard, as shown in FIG. 4, the cassettes 12 desirably include tabs 64 and notches 66 for aligned and nested reception of the cassettes 12 on the tower 18, in a vertically aligned manner with the ports 56 arranged to define the dispensing chute 62.

Figure 2:
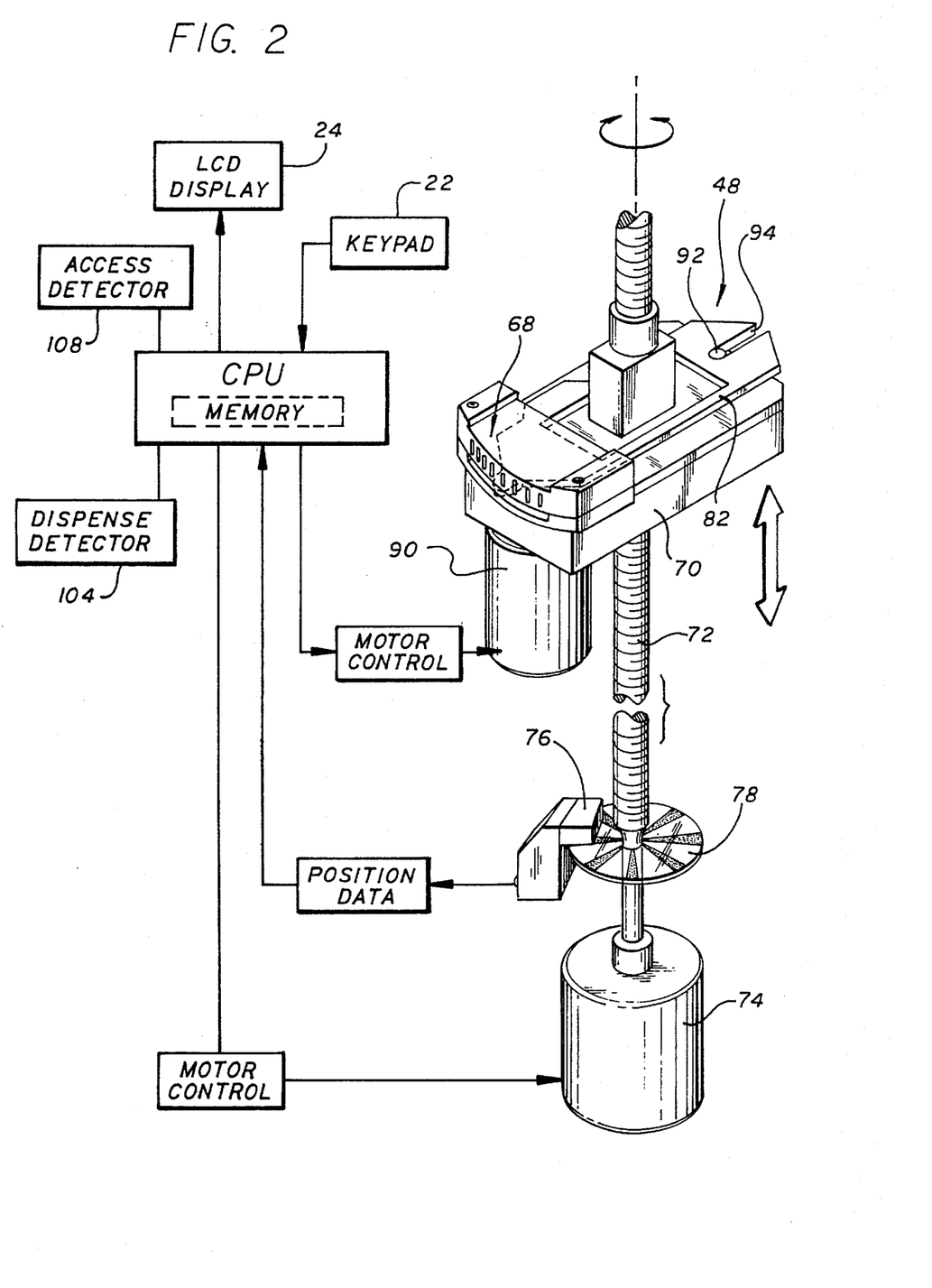
FIG. 2 is an enlarged, partially exploded perspective view depicting a station read head and station dispense head, in combination with schematic depiction of station control components.
Figure 8:
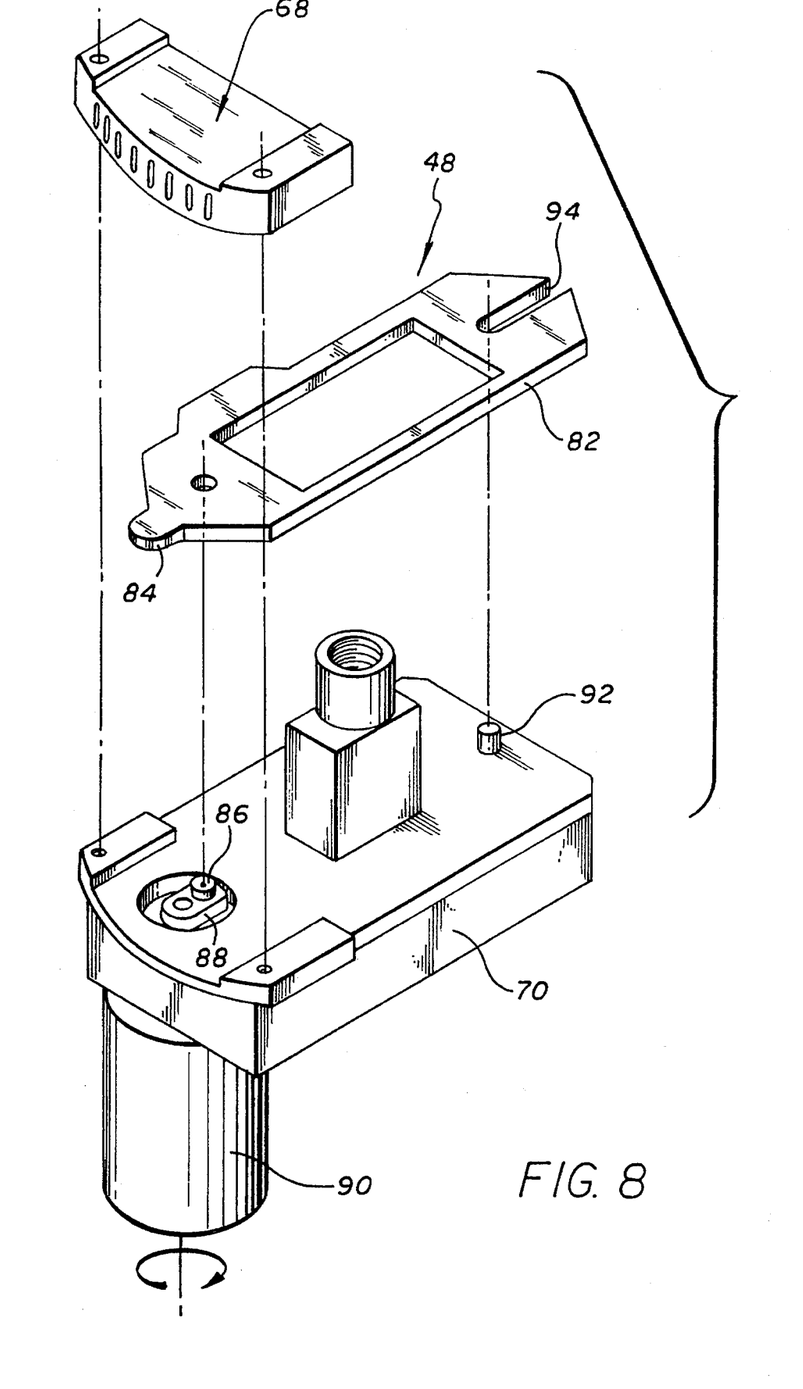
FIG. 8 is an enlarged exploded perspective view illustrating construction details of the station read head and the station dispense head.

FIGS. 2 and 8 illustrate the dispense head 48 in combination with a station read head 68. These dispense and read head structures are mounted within the tower 18, as viewed in FIGS. 9, 11 and 13, in a position for accessing the cassettes 12 loaded onto the tower via an open window 69 formed in the rear side of the tower.

More particularly, the read head 68 comprises an optical scanner mounted on an elevator plate 70 which is carried in turn for vertical displacement on a rotatable lead screw 72. A drive motor 74 is provided for rotatably driving the lead screw 72, thereby translating the elevator plate back-and-forth in a vertical direction within the cassette support tower 18. The drive motor 74 is operated by the control unit 14. A second optical sensor 76 is conveniently provided in association with a position wheel 78 which rotates with the lead screw 72 to enable the control unit 14 to track the specific vertical position of the elevator plate 70.

When the medication-containing cassettes 12 are loaded onto the cassette tower 18, the control unit 14 is signalled by a load switch 80 (FIG. 1). Thereafters the control unit 14 operates the read head 68 to traverse vertically for the purpose of reading the scannable data 54 on each one of the stacked cassettes. By this step, the control unit 14 is automatically programmed with information identifying the medication in each cassette, and the prescription schedule associated therewith. The control unit 14 can then respond to this inputted data to operate the station 10 in accordance with the prescription schedule for each mediation. Alternately, other means may be provided for detecting loading and/or unloading of the cassettes from the station, to provide for subsequent traversal of the read head 68 to read the data 54 and thereby enable the control unit to identify each medication type, location, and prescription schedule.

Figure 9:
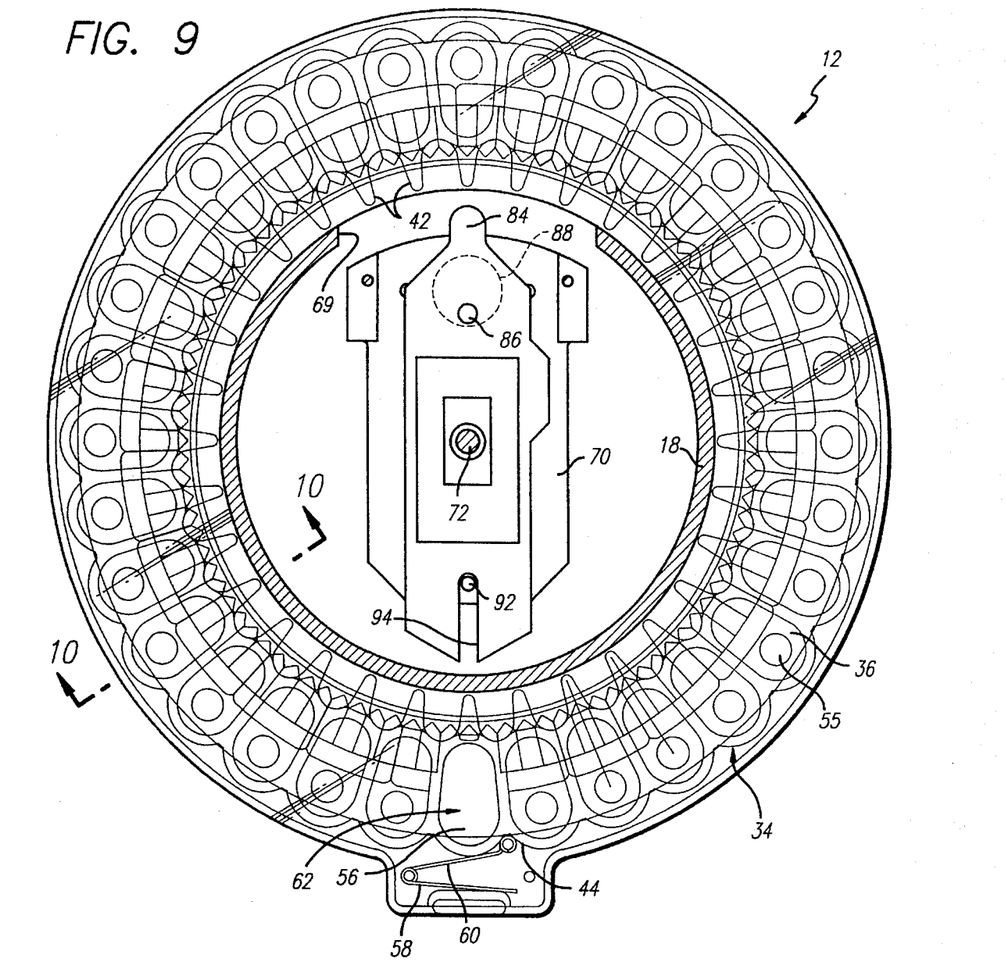
FIG. 9 is an enlarged horizontal sectional view taken generally on the line 9—9 of FIG. 1.
Figure 10:
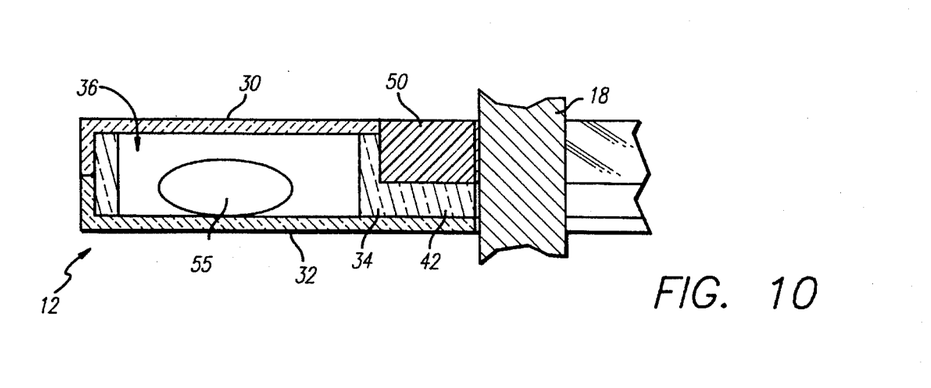
FIG. 10 is an enlarged fragmented vertical sectional view taken generally on the line 10—10 of FIG. 9.
Figure 11:
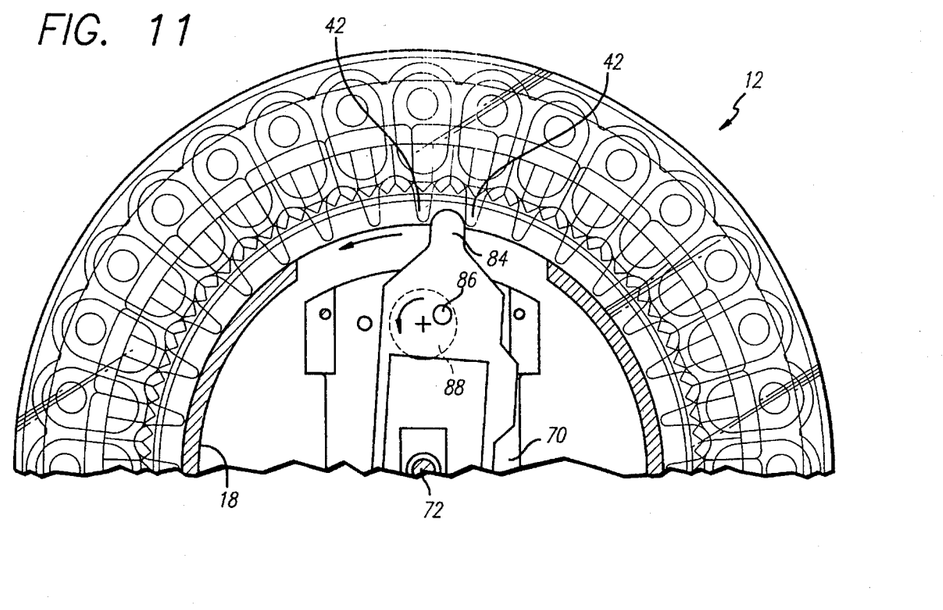
FIGS. 11 and 12 are fragmented sectional views similar to a portion of FIG. 9, and illustrating operation of the station dispense head to dispense medication from a medication-containing cassette.
Figure 12:
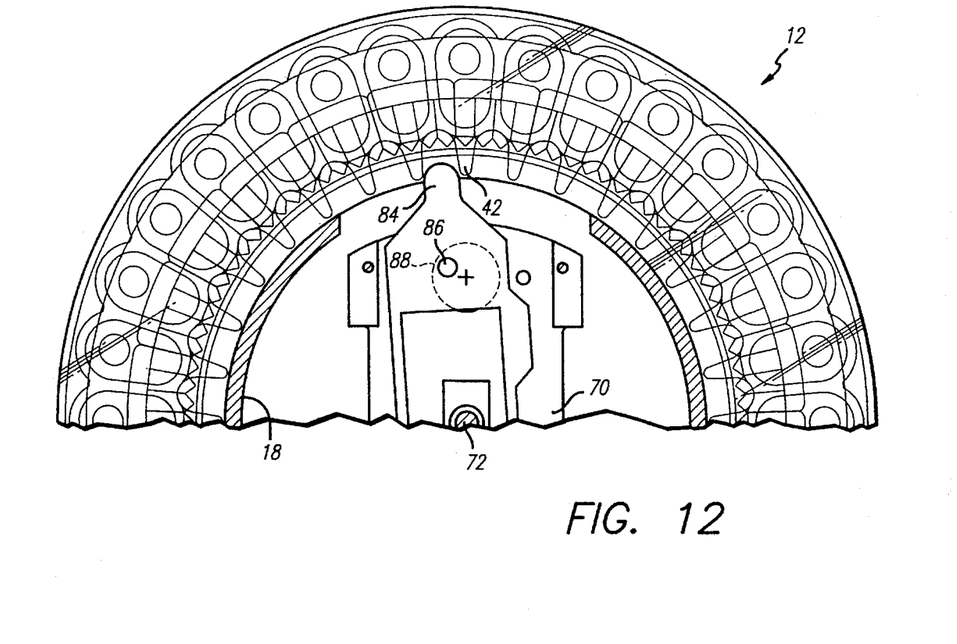

The dispense head 48 is carried on the elevator plate 70 and comprises a slide 82 having a drive lobe 84 for engaging and driving the drive teeth 42 of a cassette 12 aligned therewith. In this regard, the slide 82 is driven by a pin 86 (FIG. 8 and 9) mounted at or near the periphery of a drive cam 88 mounted on the elevator plate 70. A separate drive motor 90 is provided for rotating the drive cam 88 through a single revolution, for purposes of indexing the carousel 34 of a selected cassette through a single increment or step for the purpose of moving the next pocket 36 in succession into alignment with the dispense chute 62. As shown in FIGS. 9, 11 and 12, such indexing action occurs as the slide 82 advances with an arcuate motion into the space between a pair of drive teeth 42, and then translates the carousel 34 rotationally through a single index step, before retracting the slide 82 to its original position. A cam pin 92 on the elevator plate 70 rides in an elongated slot 94 in the slide 82 to assist in guiding slide motion to index the associated carousel, as described. This indexing motion occurs subsequent to vertical displacement of the elevator plate 70 in a manner aligning the slide 82 with a selected cassette 12 from which a medication dose is to be dispensed.

A receiver 96 is positioned at the bottom of the dispense chute 62 and permits patient access to the dispensed medication. As shown in FIGS. 5 and 6, the receiver 92 comprises a cover 98 having an aperture 99 therein in vertical alignment with the dispense chute 62. The medication dispensed falls through the aperture 99 into an upwardly open receiver cup 100, awaiting patient access. The receiver cup 100 desirably includes a sensor plate 102 adapted to detect impact of the medication therewith, and thereby provide a signal to a dispense detector 104 which forms a part of the control unit 14 and confirms proper dispensing of a desired medication dosage. If a medication dose has been dispensed but the sensor plate has not detected proper dispensing, the alarm 26 may be activated. The receiver cup 100 can be pivoted downwardly with respect to the cover 98, as viewed in FIG. 6, to permit patient access to the dispensed medication. In this regard, the receiver cup 100 is mounted on the base 16 by means of a spring-loaded pivot pin 106 or the like which urges the receiver cup 100 toward a normally closed position as viewed in FIG. 5. The cup 100 is easily pivoted downwardly (FIG. 6) for removal of the medication from the station. An access detector 108 of the control unit 14 can be signalled upon medication removal so that an appropriate dispense-and-removal record can be made and retained in the control unit memory.

In a typical environment of operation, the station base 16 and associated tower 18 are provided to a patient for convenient placement at patient bedside or other suitable location, for example, for in-home use. The keypad 22 is used to program the control unit 14 with basic information such as time of day, patient identification, alarm functions, memory and data storage functions, etc. In addition, the station can be programmed to provide a permissible time window within which medications may be dispensed early or on demand, according to specific patient requirements and daily activity schedules.

The medication-containing cassettes 12 are individually loaded by trained personnel, such as at a pharmacy, and then stacked onto the station tower 18 in any order. Loading of the cassettes 12 onto the tower may be done by the patient, without requiring the task to be done by or under supervision of trained personnel. In the currently preferred form, it is contemplated that multiple cassettes may be filled with the same medication which must be taken more than once each day. For example, for a medication prescribed at six-hour intervals, it is envisioned that four such cassettes will be provided.

At the conclusion of cassette placement onto the tower, as may be monitored by the load switch 80, the control unit 14 operates the read head 68 to traverse the stack of cassettes and read the scannable data 54. By this process, the control unit automatically identifies each mediation and its location in the stock and the applicable prescription schedule. Alternately, this data scan can be initiated manually by manipulation of the keypad 22. Thereafter, the control unit 14 automatically operates to dispense the appropriate medication at the appropriate time. For example, in the case of a medication to be taken at six-hour intervals, the dispense head will over the course of a day dispense one dose from each of the four cassettes containing that medication. Automatic operation continues unless and until cassettes are subsequently removed from or loaded onto the tower, or until an alarm is sounded in the event of one or more cassettes reaching an empty condition. The alarm may be activated by the control unit memory which may contain information regarding the number of cassette pockets 36, or otherwise by failure of the dispense detector to detector 104 medication dispensing in response to operation of the dispense head.

The improved medication dispenser station of the present invention thus provides for accurate and timely dispensing of the medications to a patient, in a system wherein accurate and reliable dispensing is substantially assured without requiring complex station programming by the patient or other untrained personnel. Instead, the patient merely loads the medication-containing cassettes 12 onto the tower 18, and the station essentially programs itself to dispense one or more medications in accordance with the appropriate schedule.

A variety of further modifications and improvements to the present invention will be apparent to those persons skilled in the art. Accordingly, no limitation on the invention is intended by way of the foregoing description and accompanying drawings, except as set forth in the appended claims.

What is claimed is:

1. A medication dispenser station, comprising:

a plurality of cassettes each for receiving a selected medication in individual doses, each of said cassettes further including scannable data identifying the medication therein and prescription schedule for administration of such medication to a patient;

a station base including means for receiving and supporting said plurality of cassettes;

read means on said base for reading said scannable data;

dispense means on said base for dispensing medication from said plurality of cassettes; and control means responsive to mounting of said cassettes onto said base for operating said read means to read said scannable data, and subsequently for operating said dispense means in response to said scannable data to dispense each medication from said cassettes in accordance with the prescription schedule associated therewith.

2. The medication dispenser station of claim 1 wherein said base includes a receiver for receiving medication dispensed by said dispensing means, and dispense detection means for detecting dispensing of medication to said receiver.

3. The medication dispenser station of claim 2 further including access detection means for detecting access to said receiver for removal of dispensed medication therefrom.

4. The medication dispenser station of claim 1 wherein each of said cassettes defines a vertically open passage, and further wherein said plurality of cassettes are arranged in a vertical stack with the vertically open passages thereof in vertical alignment to cooperatively define a vertically open dispense chute, and further including a receiver disposed at the bottom of said dispense chute.

5. The medication dispenser station of claim 1 wherein said scannable data on each of said cassettes comprises bar code data.

6. The medication dispenser station of claim 1 wherein said dispense means comprises a single dispense head, and means for displacing said dispense head into association with each of said cassettes one at a time to dispense medication therefrom.

7. A medication dispenser station, comprising:

a plurality of cassettes each for receiving a selected medication in individual doses, each of said cassettes further including scannable data identifying the medication therein and prescription schedule for administration of such medication to a patient;

a station base including means for receiving and supporting said plurality of cassettes;

read means on said base for reading said scannable data;

dispense means on said base for dispensing medication from said plurality of cassettes; and control means for operating said read means to read said scannable data, and for operating said dispense means in response to said scannable data to dispense each medication from said cassettes in accordance with the prescription schedule associated therewith;

each of said cassettes defining a vertically open passage, and further wherein said plurality of cassettes are arranged in a vertical stack with the vertically open passages thereof in vertical alignment to cooperatively define a vertically open dispense chute, and further including a receiver disposed at the bottom of said dispense chute, said plurality of cassettes further including tab and notch means for nested engagement of said cassettes in said vertical stack with said vertically open passages thereof in vertical alignment to define said dispense chute.

8. A medication dispenser station, comprising:

a plurality of cassettes each for receiving a selected medication in individual doses, each of said cassettes further including scannable data identifying the medication therein and prescription schedule for administration of such medication to a patient;

a station base including means for receiving and supporting said plurality of cassettes;

read means on said base for reading said scannable data;

dispense means on said base for dispensing medication from said plurality of cassettes; and control means for operating said read means to read said scannable data, and for operating said dispense means in response to said scannable data to dispense each medication from said cassettes in accordance with the prescription schedule associated therewith;

each of said cassettes defining a vertically open passage, and further wherein said plurality of cassettes are arranged in a vertical stack with the vertically open passages thereof in vertical alignment to cooperatively define a vertically open dispense chute, and further including a receiver disposed at the bottom of said dispense chute, each of said cassettes further comprising a generally ring-shaped housing having a rotatable carousel mounted therein and cooperating with said housing to define an annular array of pockets for receiving medication, said dispense means including a drive member for engaging said carousel to rotate said carousel within said housing through a succession of index steps to displace said pockets in succession into alignment with said vertically open passage, whereby medication within each pocket falls through the dispense chute upon pocket alignment therewith.

9. The medication dispenser station of claim 8 wherein each of said cassettes further includes spring detent means for releasibly securing said carousel in a position within said housing with one of said pockets in alignment with said vertically open passage.

10. A medication dispenser station, comprising:

a plurality of cassettes each for receiving a selected medication in individual doses, each of said cassettes further including scannable data identifying the medication therein and prescription schedule for administration of such medication to a patient;

a station base including means for receiving and supporting said plurality of cassettes;

read means on said base for reading said scannable data;

dispense means on said base for dispensing medication from said plurality of cassettes; and control means for operating said read means to read said scannable data, and for operating said dispense means in response to said scannable data to dispense each medication from said cassettes in accordance with the prescription schedule associated therewith;

said read means comprising a single read head, and means for displacing said read head successively into association with each of said cassettes to read said scannable data thereon.

11. A medication dispenser station, comprising:

a plurality of cassettes each for receiving a selected medication in individual doses, each of said cassettes further including scannable data identifying the medication therein and prescription schedule for administration of such medication to a patient;

a station base including means for receiving and supporting said plurality of cassettes;

read means on said base for reading said scannable data;

dispense means on said base for dispensing medication from said plurality of cassettes; and control means for operating said read means to read said scannable data, and for operating said dispense means in response to said scannable data to dispense each medication from said cassettes in accordance with the prescription schedule associated therewith;

said read means comprising a single read head and wherein said dispense means comprises a single dispense head, and drive means for displacing said read head and dispense head into association with each of said cassettes, one at a time, to read said scannable data and to dispense the medication.

12. The medication dispenser station of claim 11 wherein said drive means comprises an elevator having said read head and said drive head thereon, a lead screw carrying said elevator for vertical displacement relative to said cassettes, means for rotatably driving said lead screw to vertically translate said elevator, and means for monitoring the vertical position of said elevator.

13. A medication dispenser station, comprising:

a station base having an upwardly projecting cassette tower mounted thereon;

a plurality of generally ring-shaped cassettes each for receiving a selected medication in individual doses, said cassettes being adapted for mounting about said tower in a vertical stack;

each of said cassettes having a generally ring-shaped carousel mounted rotatably within a generally ring-shaped housing and cooperating therewith to define an annular array of pockets for receiving medication, said housing having a vertically open passage formed therein at a selected location whereby said passages of said plurality of cassettes cooperate to define a vertically open dispense chute when said cassettes are mounted about said tower in said vertical stack;

said carousel of each of said cassettes being rotatable within said housing to displace said pockets in succession into alignment with said dispense chute to dispense medication;

each of said cassettes further including scannable data identifying the medication therein and the prescription schedule associated therewith;

a read head within said tower for reading said scannable data on said cassettes;

a dispense head within said tower for engaging and rotating said carousels of said cassettes to dispense medication; and control means for operating said read head to read said scannable data, and for responding thereto for operating said dispense head.

14. The medication dispenser station of claim 13 further including drive means for translating said read head and dispense head into association with each of said cassettes, one at a time.

15. The medication dispenser station of claim 13 wherein said drive means comprises an elevator having said read head and said drive head thereon, a lead screw carrying said elevator for vertical displacement relative to said cassettes, means for rotatably driving said lead screw to vertically translate said elevator, and means for monitoring the vertical position of said elevator.

16. The medication dispenser station of claim 15 wherein said carousel for each of said cassettes includes a plurality of drive teeth at the inner periphery thereof, said drive means including a drive member for engaging said teeth to index said carousel.

17. The medication dispenser station of claim 16 wherein each of said cassettes further includes spring detent means for releasibly securing said carousel in a position within said housing with one of said pockets in alignment with said vertically open passage.

18. The medication dispenser station of claim 17 wherein said carousel of each of said cassettes has a scalloped outer periphery defining a succession of detents, and wherein said spring detent means comprises a spring reacting between said housing and said detents.

19. The medication dispense station of claim 13 further including a receiver at the bottom of said dispense chute, and dispense detention means for detecting dispensing of medication to said receiver.

20. The medication dispenser station of claim 19 further including access detection means for detecting access to said receiver for removal of dispensed medication therefrom.

21. The medication dispenser station of claim 13 wherein said control unit includes means responsive to mounting of said cassettes onto said tower for operating said read head to read said scannable data.

22. The medication dispenser station of claim 13 wherein said plurality of cassettes include tab and notch means for nested engagement of said cassettes in said vertical stack with said vertically open passages thereof in vertical alignment to define said dispense chute.

23. A method of dispensing medication, comprising the steps of:

loading selected medication in individual doses into a plurality of cassettes;

applying scannable data to said cassettes to identify the medications and prescription schedules associated therewith;

mounting said cassettes in a vertical stack;

reading the scannable data with a read head and loading said data into a control unit memory, said reading step comprising translation of the read head successively into association with each of said cassettes; and thereafter responding to the data loaded into the control unit memory to operate a dispense head to dispense the medications from the cassettes in accordance with the prescription schedules associated therewith, said step of operating the dispense head comprising moving the dispense head into association with each of said cassettes, one at a time.

* * * * *